Figure 1A:
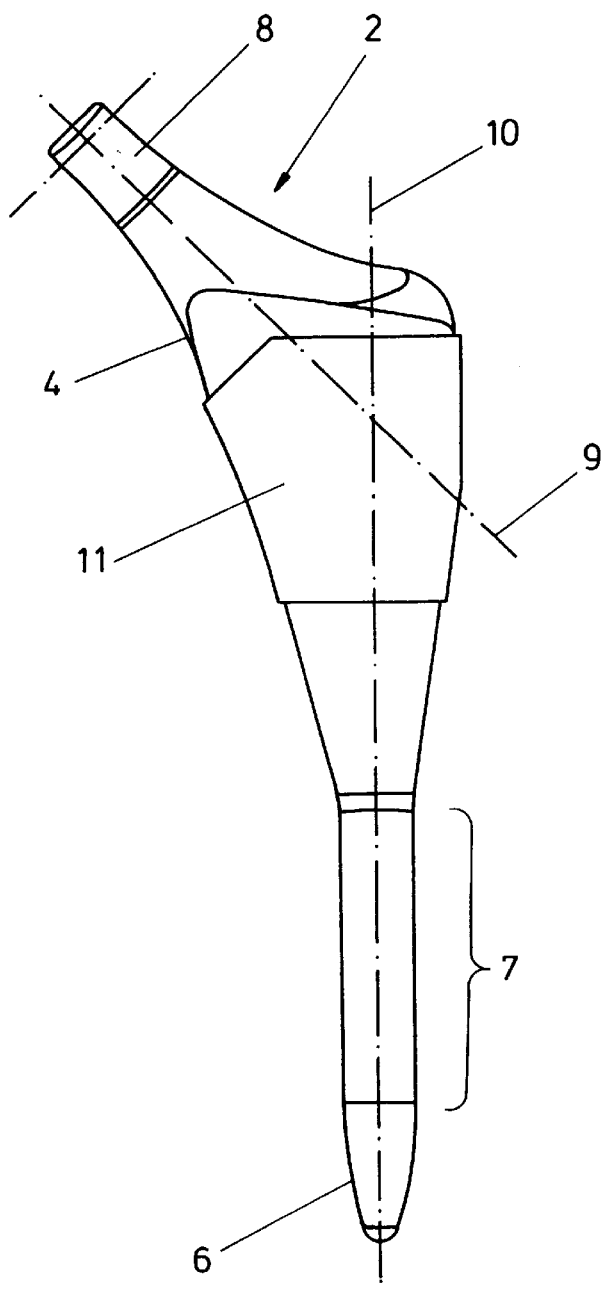

United States Patent
Cohen

Patent Number: 6,045,556
Date of Patent: Apr. 4, 2000

[54] BROACH FOR SHAPING A MEDULLARY CAVITY IN A BONE

[75] Inventor: Andrew Cohen, Beal, Goole, United Kingdom

[73] Assignee: Depuy International, Ltd., United Kingdom

[21] Appl. No.: 09/297,752

[22] PCT Filed: Nov. 7, 1997

[86] PCT No.: PCT/GB97/03069

§ 371 Date: May 5, 1999

§ 102(e) Date: May 5, 1999

[87] PCT Pub. No.: WO98/20800

PCT Pub. Date: May 22, 1998

[30] Foreign Application Priority Data

Nov. 8, 1996 [GB] United Kingdom ............... 5623294

[51] Int. Cl.⁷ .................................................. A61B 17/16
[52] U.S. Cl. ............................................. 606/85; 606/79
[58] Field of Search ............................. 606/79, 80, 81, 606/84, 85

[56] References Cited

U.S. PATENT DOCUMENTS

| | | | |
|---|---|---|---|
| 5,006,121 | 4/1991 | Hafeli | 606/85 |
| 5,089,004 | 2/1992 | Averill et al. | 606/85 |
| 5,441,501 | 8/1995 | Kenyon | 606/85 |

FOREIGN PATENT DOCUMENTS 0 359 097  3/1990  European Pat. Off. .

*Primary Examiner*—Michael Buiz
*Assistant Examiner*—Daphnn Shai
*Attorney, Agent, or Firm*—Madson & Metcalf

[57] ABSTRACT

A broach for shaping a medullary cavity in a bone to receive an orthopaedic prosthesis which is tapered inwardly in a direction from its proximal end toward its distal end. The broach has (a) a proximal portion on which a plurality of cutting teeth are arranged to cut the internal surface of the cavity to receive the broadened proximal portion of the prosthesis, (b) a plug portion at or towards the distal end of the broach, and (c) an elongate connecting portion by which the plug portion is connected to the proximal portion. The transverse dimension of the connecting portion is less than that of the plug portion and the proximal portion, and the width of the plug portion is greater at a point between its ends than at any other point along its length, the surface at the point of greatest width being convex when the broach is viewed from the side.

14 Claims, 3 Drawing Sheets

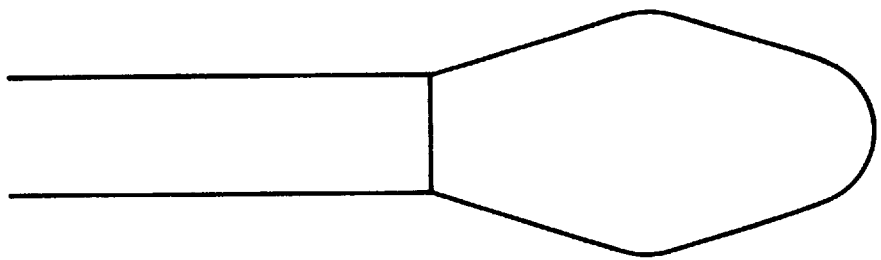
FIG. 3E
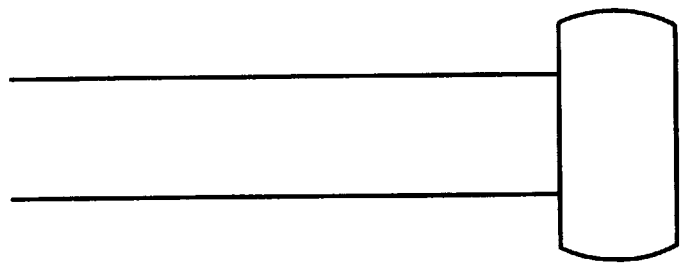
FIG. 3D
FIG. 3
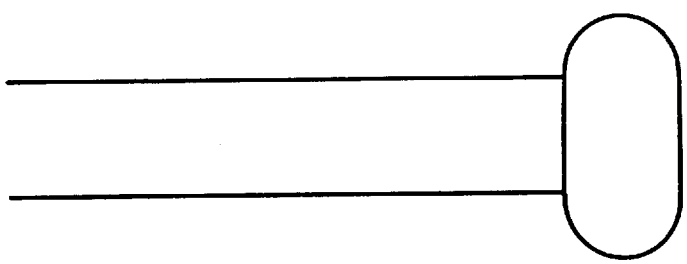
FIG. 3C
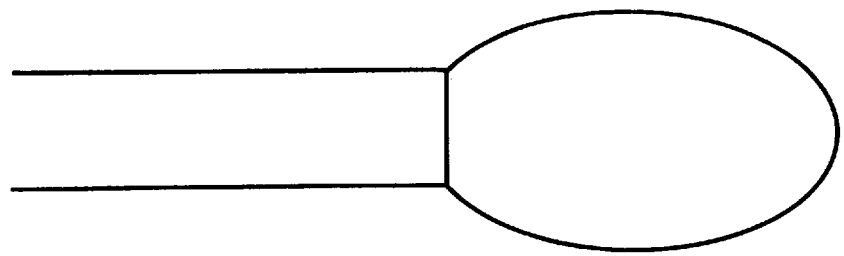
FIG. 3B
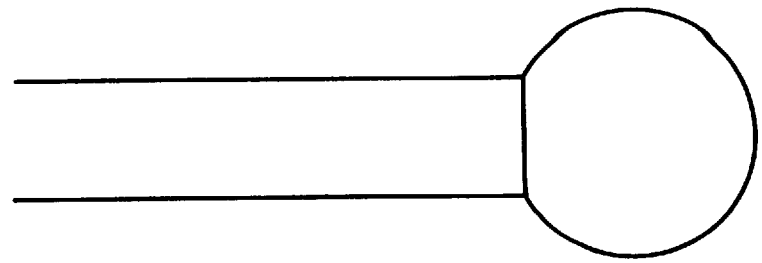
FIG. 3A

BROACH FOR SHAPING A MEDULLARY CAVITY IN A BONE

This invention relates to a broach for shaping a medullary cavity in a bone and to a method of shaping the cavity.

An artificial joint component can be connected to the resected end of a bone by means of a tapered portion which can be received in the medullary cavity of the bone. In order to obtain a strong connection between the component and the internal surface of the cavity, it is important to ensure that the surfaces of the component and the cavity match so that there is contact between the surfaces over large proportions of their areas, over substantially the entire area of the prosthesis in some cases or over selected portions of its area in other cases. The connection between the bone and the prosthesis can then be created by ingrowth of bone tissue or by means of a bone cement.

Preparation of the bone cavity can be achieved using tools such as reamers and broaches. A reamer is a rotating tool which can be used to create a cavity with a circular cross-section, which will frequently be constant along its length. A broach is generally manipulated in an axial direction. It can be used to create a cavity with a non-circular cross-section. It is suitable for creation of the portion of a medullary cavity that is to receive the tapered portion of a prosthesis, in particular to ensure that the tapered shape of the prosthesis, which can be a complicated irregular shape, is properly matched by the shape of the internal surface of the bone cavity.

A difficulty with use of a broach to shape a bone cavity can lie in ensuring that the broach is properly aligned with the axis of the cavity. Misalignment of the broach can result in the shape of the proximal portion of the cavity matching the shape of the broach but with the axis in the proximal portion being misaligned with the axis in the remainder of the cavity. A result of this can be that the actual degree of matching between the cavity and the prosthesis is reduced in the proximal portion of the cavity, when the prosthesis bercomes aligned with the distal portion.

The present invention provides a broach with a proximal cutting portion having a broadened cross-section and a plug portion, spaced apart from the cutting portion and connected to it by means of a reduced cross-section connecting portion.

Accordingly, in one aspect, the invention provides a broach for shaping a medullary cavity in a bone to receive an orthopaedic prosthesis which is tapered inwardly in a direction from its proximal end towards its distal end, the broach having (a) a proximal portion on which a plurality of cutting teeth are arranged to cut the internal surface of the cavity to receive the broadened proximal portion of the prosthesis, (b) a plug portion at or towards the distal end of the broach, and (c) an elongate connecting portion by which the plug portion is connected to the proximal portion, in which the transverse dimension of the connecting portion being less than that of the plug portion and the proximal portion, and the width of the plug portion being greater at a point between its ends than at any other point along its length, the surface at the point of greatest width being convex when the broach is viewed from the side.

The broach of the invention can be inserted into a bone cavity which has been reamed to a diameter in which the plug portion at the distal end of the broach is a sliding fit with the internal cavity surface. The sliding fit then helps to define the axis of the cavity for the subsequent shaping of the proximal portion of the cavity by means of the cutting teeth on the broach. The broach of the invention therefore facilitates more accurate shaping of a bone cavity, particularly in the proximal region where the cavity has its largest cross-section. This can be especially important when the connection between the prosthesis and natural bone tissue is made only in the proximal region (whether the connection is made by means of bone ingrowth or using bone cement).

The connecting portion of the broach will generally be distinguishable from the proximal portion by the absence of cutting teeth. Preferably, the connecting portion has a constant cross-section along part of its length, preferably along all of its length. Preferably, the ratio of the length of the connecting portion to its transverse dimension is at least about 2, more preferably at least about 3.

The connecting portion of the broach will generally be substantially straight, so as to coincide with the axis of the bone in which the cavity is to be formed and with the axis of the prosthesis when subsequently inserted into the cavity.

The surface of the plug portion at the point of greatest width will be convex when viewed from one side, generally along one or preferably both of the anterior-posterior and medial-lateral axes. For example, when viewed from one side, the plug portion might have a generally round shape (especially a circular shape), a barrel-like shape, or a generally oval shape (with the major axis in line with the axis of the bone or transverse to it). The plug portion will normally be generally rounded, around the axis of the broach or on its end face or, preferably both. For example, the plug portion can have a circular cross-section when viewed along the axis of the connecting portion (taken perpendicular to that axis), at least at the point of its greatest width. This is particularly suitable for use in a bone cavity which has a rounded shape, for example as resulting from the use of a reamer to form the cavity. It is particularly preferred that the plug portion is substantially spherical. This facilitates movement of the broach during the cutting action, while still maintaining a pre-determined relationship between the axis of the cavity and the cut internal surface of the proximal portion of the cavity.

The transverse dimension of the plug portion will be selected according to the transverse dimension of the cavity which is to be shaped. Generally, the cavity will have a constant, circular cross-section resulting from it having been formed by reaming medullary bone tissue, preferably exposing cortical bone tissue along at least a part of the length of the bone. The plug portion will then be selected to as to be a sliding fit with the internal surface of the bone cavity, preferably being as large as possible while still being able to slide in the cavity. The selection of a plug portion that is as large as possible minimises transverse movement of the distal end of the broach in the cavity during the cutting movement of the broach at the proximal end.

Preferably, the broach of the invention is modular. For example, it can include separable proximal and plug portions. The connecting portion can be formed with either the proximal portion or the plug portion, or it can be formed as another separable portion. A modular broach has the advantage of enabling a broach to be assembled whose configuration enables a cavity to be formed to suit a particular bone structure or prosthesis or both. For example, characteristics of the broach which can be selected include the transverse dimension of the plug portion, the transverse dimension and overall configuration of the proximal portion, and the length of the connecting portion. A broach kit might include plug portions with transverse dimensions ranging from 6 mm to 15 mm, in steps of 0.75 to 1.5 mm.

Preferably, the broach has formations at its upper end to engage a suitable handle, by which it can be manipulated to cut the bone tissue in contact with its cutting teeth. A suitable combination of formations is disclosed in WO-A-95/22286.

In another aspect, the invention provides a method of shaping a medullary cavity in a bone to receive an orthopaedic prosthesis which is tapered inwardly in a direction from its proximal end towards its distal end, which comprises:

(a) reaming a cavity in the medullary tissue of the bone, (b) inserting a broach into the reamed cavity, the broach having a proximal portion on which a plurality of cutting teeth are arranged to cut the internal surface of the cavity to receive the broadened proximal portion of a prosthesis, a plug portion at or towards the distal end of the broach which is a snug fit in the reamed cavity, and an elongate connecting portion by which the plug portion is connected to the proximal portion, the transverse dimension of the connecting portion being less than that of the plug portion and the proximal portion, and the width of the plug portion being greater at a point between its ends than at any other point along its length, the surface at the point of greatest width being convex when the broach is viewed from the side, and (c) moving the broach relative to the bone to cause the cutting teeth on the proximal portion of the broach to cut bone tissue that they are in contact with, so as to shape the cavity.

Examples of applications for the broach of the present invention include the shaping of a cavity in a humerus to receive a component of a replacement shoulder joint, and the shaping of a cavity in a femur to receive a component or a replacement hip joint.

Figure 2:
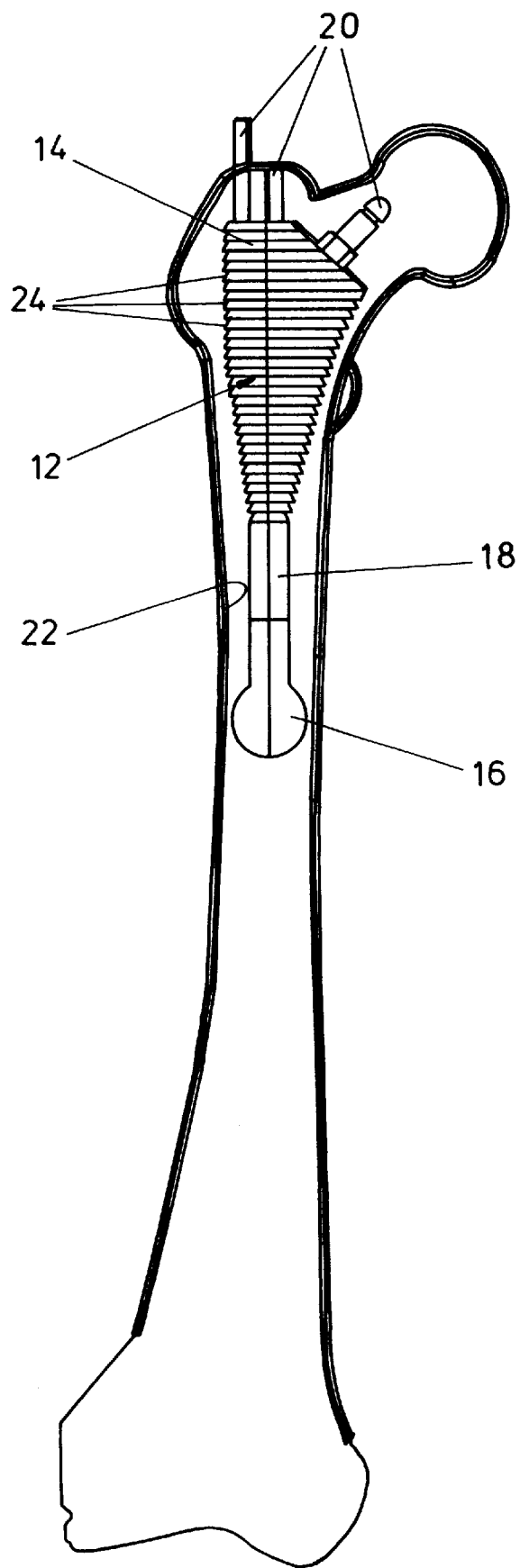

The present invention will now be described, by way of example only, with reference to the accompanying drawings, in which:

FIGS. 1(a) and (b) are anterior-posterior and medial-lateral views of the femoral component of a hip prosthesis, FIG. 2 is a transverse view, partially in section, through a part of a femur, in which a broach according to the invention is located, and FIG. 3 shows configurations of plug portions for use in the broach according to the invention.

Figure 1B:
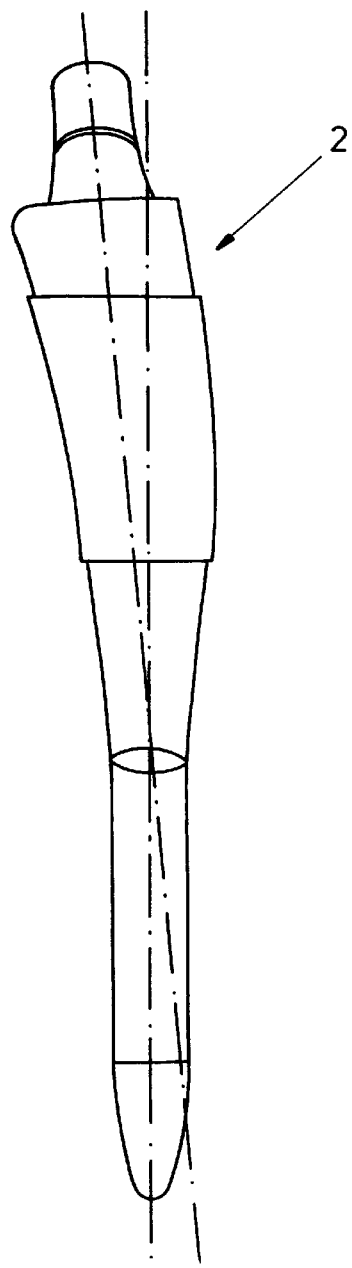

Referring to the drawings, FIG. 1 shows a femoral component 2 of a hip prosthesis. The component is tapered inwardly from its proximal end 4 towards its distal end 6. The prosthesis has a uniform cross-section over a portion 7 of its length towards the distal end. It defines an axis for the prosthesis which, when the prosthesis is in use, is aligned with the medullary axis of the femur.

A spherical bearing surface is provided on the lug 8 at the proximal end of the prosthesis. The axis 9 of the spherical surface is offset relative to the medullary axis 10 of the prosthesis, as is widely known.

It is important for accurate load transfer from the femoral component to the natural bone tissue of the resected femur that the contacting surfaces of the component and the femur be accurately matched. It is generally particularly important for the surfaces to be accurately matched in the broadened proximal region of the prosthesis. Indeed, in the case of some prosthesis, all of the load transfer between the prosthesis and the femoral bone tissue takes place through the broadened proximal portion 4 of the prosthesis (for example the region 11 of the prosthesis shown in FIG. 1): the distal portion 6 is arranged to be a loose fit in the medullary cavity of the bone.

In this latter arrangement in which load transfer takes place largely or exclusively through the proximal portion of the prosthesis, the connection between the prosthesis and the bone tissue will be formed in this region. For example, the surface of the prosthesis can be made porous, to facilitate ingrowth of bone tissue.

The broach of the invention facilitates the accurate matching of the shape of the femoral component 2 in its proximal portion 4 with the shape of the internal surface of the medullary cavity in a bone. A first stage in the preparation of a cavity involves the use of a rotating reamer tool to form a bore in the bone which has a constant cross-section. The bore formed by the reamer will follow the axis of the bone.

A broach is then used to form the enlarged proximal portion of the bone cavity. The broach 12 is constructed using modular components, as shown in FIG. 2. The broach comprises an enlarged proximal portion 14, a plug portion 16 and connecting portion 18. These three separable components are selected according to the configuration of the patient's bone, and of the prosthesis to be fitted to that bone. The plug portion 16, being generally spherical, will be selected to be a snug, sliding fit in the bone cavity resulting from the use of the reamer. The proximal portion 14 of the broach will be selected with a configuration which matches that of the prosthesis. The connecting portion will be selected with an appropriate length having regard to the length of the reamed cavity in the bone. The components of the broach can be connected to one another by appropriate formations, for example by means of appropriate screw threads.

The broach has appropriate formations 20 at its proximal end which enable it to be connected to an appropriate handle by which the broach can be manipulated, in particular while it is being used to cut bone tissue.

In use, the broach is inserted into the reamed cavity of the femur or other bone in which a prosthesis is to be disposed. The spherical plug portion 16 is slid down the reamed cavity until the broadened proximal portion 14 of the broach contacts the internal surface 22 of the bone cavity, towards the proximal end of the bone. Cutting teeth 24 on the proximal portion of the broach can then be used to cut the bone tissue. The configuration of the proximal portion of the broach ensures that the cut bone has a configuration which matches that of the prosthesis to be inserted into the cavity after the broach cutting process has been completed.

FIG. 3 shows alternative shapes of plug portions which can be incorporated in the broach shown in FIG. 2. All of the plug portions have a width that is greater at a point between its ends than at any other point along its length, and the surface at the point of greatest width is convex when the broach is viewed from the side as in the drawing. Generally, the shape of the plug portion will be substantially constant when viewed from all sides.

FIG. 3A shows a generally rounded plug portion as incorporated in the broach shown in FIG. 2. FIG. 3B shows a plug portion which is generally oval with the major axis in line with the axis of the bone in which the broach is to be used. FIG. 3C shows a plug portion which is generally oval with the minor axis in line with the axis of the bone in which the broach is to be used. FIG. 3D shows a plug portion which is generally barrel shaped. FIG. 3E shows a plug portion which is generally kite shaped along its side edges and rounded at the distal tip.

I claim:

1. A broach for shaping a medullary cavity in a bone to receive an orthopaedic prosthesis which is tapered inwardly in a direction from its proximal end towards its distal end, the broach having (a) a proximal portion on which a plurality of cutting teeth are arranged to cut the internal surface of the cavity to receive the broadened proximal portion of the prosthesis, (b) a plug portion at or towards the distal end of the broach, and (c) an elongate connecting portion by which the plug portion is connected to the proximal portion, in which the transverse dimension of the connecting portion being less than that of the plug portion and the proximal portion, and the width of the plug portion being greater at a point between its ends than at any other point along its length, the surface at the point of greatest width being convex when the broach is viewed from the side.

2. A broach as claimed in claim 1, in which the connecting portion has a constant cross-section, along at least part of its length.

3. A broach as claimed in claim 2, in which the ratio of the length of the connecting portion to its transverse dimension is at least about 2.

4. A broach as claimed in 3, in which the connecting portion is substantially straight.

5. A broach as claimed in 4, in which the ratio of the transverse dimension of the plug portion to that of the connecting portion is at least about 1.3.

6. A broach as claimed in 5, in which the cross-section of the plug portion is generally circular when viewed along the axis of the connecting portion, at least at the point of its greatest width.

7. A broach as claimed in claim 6, in which the plug portion is substantially spherical.

8. A broach as claimed in claim 7, in which the shape of the plug portion when viewed from the side is substantially constant irrespective of the angle from which it is viewed.

9. A broach as claimed in claim 1, in which the ratio of the length of the connecting portion to its transverse dimension is at least about 2.

10. A broach as claimed in claim 1, in which the connecting portion is substantially straight.

11. A broach as claimed in claim 1, in which the ratio of the transverse dimension of the plug portion to that of the connecting portion is at least about 1.3.

12. A broach as claimed in claim 1, in which the cross-section of the plug portion is generally circular when viewed along the axis of the connecting portion, at least at the point of its greatest width.

13. A broach as claimed in claim 1, in which the plug portion is substantially spherical.

14. A broach as claimed in claim 1, in which the shape of the plug portion when viewed from the side is substantially constant irrespective of the angle from which it is viewed.

* * * * *